United States Patent
Tijoe

(10) Patent No.: US 6,664,392 B2
(45) Date of Patent: Dec. 16, 2003

(54) PROCESS FOR THE PREPARATION OF MELAMINE

(75) Inventor: Tjay T. Tijoe, Sittard (NL)

(73) Assignee: DSM N.V., Heerlen (NL)

( * ) Notice: Subject to any disclaimer, the term of this patent is extended or adjusted under 35 U.S.C. 154(b) by 0 days.

(21) Appl. No.: 10/116,757

(22) Filed: Apr. 5, 2002

(65) Prior Publication Data

US 2003/0004343 A1 Jan. 2, 2003

Related U.S. Application Data

(63) Continuation of application No. PCT/NL00/00646, filed on Sep. 12, 2000.

(30) Foreign Application Priority Data

Oct. 5, 1999 (NL) .............................................. 1013217

(51) Int. Cl.$^7$ ...................... C07D 251/60; C07D 251/62
(52) U.S. Cl. ....................................... 544/201; 544/203
(58) Field of Search .................................. 544/201, 203

(56) References Cited

FOREIGN PATENT DOCUMENTS

EP          0 808 836 A1  *  11/1997
WO          WO-97 20826 A1  *  6/1997

* cited by examiner

Primary Examiner—Mukund J. Shah
Assistant Examiner—Venkataraman Balasubramanian
(74) Attorney, Agent, or Firm—Pillsbury Winthrop LLP

(57) ABSTRACT

Process for the preparation of melamine comprising a reaction step, a gas/liquid separation step in which a melamine melt is separated from off-gases, a stripping step and a cooling step, in which the stripping step is carried out at a pressure of between 5 MPa and 17 MPa and a temperature of between 330° C. and 450° C. and in which the melamine melt obtained in the preceding steps is pressurised in the cooling step to a pressure of between 15 and 35 MPa, with the pressure in the cooling step being higher than the pressure in the stripping step and with the temperature in the cooling step being adjusted between the melting point of the urea melt at the prevailing pressure and 365° C.

7 Claims, No Drawings

PROCESS FOR THE PREPARATION OF MELAMINE

This is a Continuation of International Application No. PCT/NL00/00646 filed Sep. 12, 2000, which designated the U.S.

The invention relates to a process for the preparation of melamine comprising a reaction step, a gas/liquid separation step in which a melamine melt is separated from off-gases, a stripping step and a cooling step.

Such a process is disclosed in WO 97/20826. That publication teaches that melamine is prepared by separating, in a gas/liquid separation step, a melamine melt, which preferably has been prepared from urea in a non-catalytic reaction step in a high-pressure reactor, from released gases, and by subsequently treating the melt with $NH_3$ in a stripping step in order to reduce the amount of $CO_2$ dissolved in the melamine melt. Next, the melamine melt with the $NH_3$ dissolved in it is cooled, at a pressure of between 5 and 40 MPa, in a cooling step to a temperature of between 0 and 60° C. above the melting point at the prevailing ammonia pressure but below 350° C. and then expanded to produce solid melamine and then further cooled. In the examples described in WO 97/20826 in which high-purity melamine is obtained, the process pressure $p_1$ in the melamine melt during the cooling step is always 20 MPa or higher. The highest purities are obtained in those examples in which the process pressure $p_1$ is 25 MPa or higher. In the process according to WO 97/20826, the process pressure in the reaction step, the gas/liquid separation step and the stripping step is preferably the same as the pressure in the cooling step.

A drawback of the known process is that the pressure in a large part of the preparation process, in particular in the stripping step, needs to be maintained at a very high level, in the light of the examples preferably higher than 20 MPa, in order to obtain melamine with a high purity. The investment costs of process plants are known to increase with increasing plant operating pressure. Thus, the known process leads to relatively high investment costs as far as the required process equipment is concerned. It is also known that the operating costs of a process plant increase strongly with increasing plant operating pressure. Thus, the known process also leads to relatively high operating costs.

The object of the invention is to largely avoid the aforementioned drawbacks by a process that yet produces melamine of high purity.

Said object is achieved by the stripping step being operated at a pressure of between 5 MPa and 17 MPa and a temperature of between 330° C. and 450° C. and by the melamine melt obtained in the preceding steps being pressurised in the cooling step to a pressure of between 15 MPa and 35 MPa, with the pressure in the cooling step being higher than the pressure in the stripping step and with the temperature in the cooling step being adjusted between the melting point of the melamine melt at the prevailing pressure and 365° C.

Due to the lower pressure in the stripping step than in the process according to WO 97/20826, the process of the invention allows the equipment in which the stripping step is effected to be of less heavy construction.

Despite the relatively low pressures in the stripping step, the eventually obtained melamine is of very high purity: the percentage of undesirable compounds such as ammeline, ammelide, cyanuric acid, melem and melam is very low. This is surprising and cannot be derived from WO 97/20826, which states that it is optimum for the stripping step to be conducted at the same high pressure as the cooling step if high-purity melamine is to be obtained. Surprisingly, the amounts of stripping medium per kg of melamine needed in the stripping step are also lower when the step is carried out at a lower pressure between 5 MPa and 17 MPa.

In the off-gas released in the stripping step there is present, besides the stripping medium and the $CO_2$ released, an amount of evaporated melamine. Such melamine vapour needs to be removed from the off-gas in a scrubbing step. An added advantage of the process of the invention is that, because of the smaller amounts of required stripping medium, less melamine vapour is released in the stripping step per unit time than in the known process. As a result, less melamine needs to be scrubbed per unit time so that the scrubbing step may be of simpler design.

As a consequence, both the investment costs and the operating costs of a high-purity melamine plant according to the process of the invention are substantially lower than in the known process.

EP-A-0808836 discloses a process for the preparation of melamine which comprises a stripping step and a cooling step in which the stripping step is effected in a $CO_2$ remover and the cooling step is effected in a mixing vessel. EP-A-0808836 does not teach, however, under what conditions the stripping step should be effected. Nor does EP-A-0808836 teach how the relationship in operating conditions between the stripping step and the cooling step should be chosen. Lastly, EP-A-0808836 fails to show that the advantages of the process of the invention may be achieved.

The preparation of melamine normally starts from urea, in the form of a melt, as a raw material. $NH_3$ and $CO_2$ are by-products during the preparation of melamine, which proceeds according to the following reaction equation:

$$6\ CO(NH_2)_2 \rightarrow C_3N_6H_6 + 6\ NH_3 + 3\ CO_2$$

The preparation may be effected in a high-pressure process known per se, in which melamine is prepared without the presence of a catalyst and with pressure normally being between 5 and 50 MPa. The temperature at which the reaction is effected is between 325 and 450° C. The by-products $NH_3$ and $CO_2$ are customarily returned to an adjacent urea plant.

As a rule, a high-pressure process includes a scrubber unit, a reactor, a gas/liquid separator, a stripper and/or an after-reactor or ageing vessel, one or more cooling vessels or mixing vessels and an expansion vessel.

It is possible for some vessels to be combined into a single vessel. Examples are a combination of the reactor with the gas/liquid separator, a combination of the gas/liquid separator with the stripper or a combination of stripper and cooling vessel.

In an embodiment of the high-pressure process, melamine is prepared from urea in for example a plant consisting of a scrubber unit, a reactor for the preparation of melamine, a gas/liquid separator, a stripper, a cooling vessel and an expansion vessel.

For effecting the scrubbing step, a scrubber unit is supplied with urea melt from a urea plant at a pressure of 5 top 50 MPa and at a temperature above the melting point of urea.

In the scrubber unit the liquid urea comes into contact with off-gases from the gas/liquid separator and from the stripper.

The off-gases essentially consist of $CO_2$ and $NH_3$ and also contain an amount of melamine vapour. The molten urea scrubs the melamine vapour out of the off-gas and carries this melamine back to the reactor so that the evaporated melamine is not lost. At the same time, the temperature of the urea is increased.

The off-gases are discharged from the top of the scrubber unit and are preferably returned to a urea plant for use as a raw material for urea production.

In order to carry out the reaction step, the preheated urea, which contains the scrubbed melamine, is passed from the scrubber unit to the reactor, which has a pressure of 5 to 50 MPa. The urea melt may be transferred to the melamine reactor with the aid of gravity by placing the scrubber unit above the reactor. An amount of $NH_3$ in the form of for example a liquid or hot vapour, may be metered to the reactor. The $NH_3$ added may serve as for example a purifying agent to prevent blockage of the reactor bottom or to prevent the formation of melamine condensation products such as melam, melem and melon or to promote mixing in the reactor.

In the reactor, the molten urea is heated to a temperature of 325 to 450° C. at the above-mentioned pressure, in which conditions the urea is converted into liquid melamine, $CO_2$ and $NH_3$.

In order to carry out the gas/liquid separation step, the reaction product, essentially consisting of melamine and of $CO_2$ and $NH_3$ evolving in the reaction, is passed to a gas/liquid separator downstream of the reactor.

The off-gases, which in this step essentially consist of $CO_2$, $NH_3$ and evaporated melamine, are separated from the liquid melamine and are passed to the scrubber unit in order to remove the melamine vapour present in the off-gases and to preheat the urea melt.

The liquid reaction product, a melamine melt essentially consisting of liquid melamine with $CO_2$ and $NH_3$ dissolved in it, is supplied to the stripper.

In order to carry out the stripping step, a stripping gas, normally $NH_3$, is metered to the stripper. The stripping gas strips dissolved $CO_2$ from the melamine melt, with at the same time an amount of melamine vapour being carried along by the stripping gas. Another object of stripping $CO_2$ from the melamine melt is to prevent the formation of oxygen-containing compounds as by-products. Examples of oxygen-containing compounds are ammeline, ammelide and cyanuric acid. The amount of stripping gas metered to the stripper normally is 0.02 to 3 tonnes of stripping gas per tonne of melamine.

In the process of the invention, the pressure in the stripper is adjusted to between 5 and 17 MPa and the temperature between 330° C. and 450° C. In the process of the invention it suffices to meter to the stripper 0.02 to 2 tonnes of stripping gas per tonne of melamine melt. In this way, the amount of oxygen-containing compounds in the melamine melt may be limited to less than 0.7% by weight.

The flow rate of the stripping gas and the cross-sectional area of the stripper are preferably so chosen that the superficial gas velocity relative to the total stripper cross-sectional area is between 0.001 and 0.2 m/s, preferably between 0.003 and 0.1 m/s. By superficial gas velocity is meant the volume flow rate of the stripping gas in $m^3$/s divided by the stripper cross-sectional area in $m^2$.

It is preferred for the stripper to be operated with a liquid hold-up in excess of 35%. Liquid hold-up is defined as follows: (dynamic liquid volume in the stripping zone)/(volume of the stripping zone)

The dynamic liquid volume is the total liquid volume minus the static liquid volume. (For experimental determination, refer to H. Z. Kister, Dilstillation-design, McGraw-Hill (1992), Section 8.2.14). The stripping zone is the area in the stripper between the point where the stripping gas first comes into contact with the liquid and the point where the stripping gas has last been in contact with the liquid.

More preferably, the liquid hold-up in the stripper is in excess of 50%, even more preferably in excess of 70%.

If desired, the melamine melt may be cooled to some extent already during the stripping step so that the cooling step may proceed more rapidly.

As is the case with the off-gas from the gas/liquid separator, the off-gas released from the stripper may be passed to the scrubber unit for removing melamine vapour and for preheating the urea melt. It is also possible to pass the off-gas from the stripper to a separate, second scrubber unit.

The melamine melt, whose temperature is between the melting point of the melamine melt and 450° C., is passed to a cooling vessel.

In the process of the invention, in order to carry out the cooling step, the melamine melt in the cooling vessel is pressurised to between 15 and 35 MPa, preferably by adding extra $NH_3$, with the pressure in the cooling step always being higher than the pressure in the stripping step.

The stripping step is preferably carried out at a pressure which is at least 1.5 MPa below the pressure in the cooling step; more preferably, the stripping step is carried out at a pressure which is at least 5 MPa below the pressure in the cooling step. This presents the advantage that both the stripping step and the cooling step may be operated to a greater extent within the optimum pressure range of each step. The cooling vessel normally includes means of preparing a homogeneous, ammonia-containing melamine melt. The additional $NH_3$ supplied dissolves in the melamine melt. In general, an amount of $NH_3$ is supplied such that the melamine melt becomes saturated; here, it holds that the melamine melt can absorb more $NH_3$ at higher $NH_3$ pressures.

The temperature of the melamine melt is adjusted to between the melting point of the melamine melt at the prevailing pressure and 365° C. The value of the melting point of a melamine melt saturated with $NH_3$ is affected by the amount of dissolved $NH_3$ and so by the $NH_3$ pressure: the higher the $NH_3$ pressure, the lower the melting point. As described in WO 97/20826, if for example the $NH_3$ pressure is 15 MPa, the melting point of a melamine melt saturated with $NH_3$ is approx. 330° C.; if the $NH_3$ pressure is 35 MPa, the melting point of a melamine melt saturated with $NH_3$ is approx. 295° C. The object of the cooling step is to ensure that any condensation products of melamine, such as melam and melem, are reconverted into melamine. Also, in an expansion step which normally follows the cooling step, because of the lower temperature, the melamine will solidify more rapidly inasmuch as a proportion of the heat has already been discharged.

The residence time of the melamine melt in the cooling step is between 1 minute and 10 hours.

It is preferred for the cooling step to be carried out in two or more cooling vessels arranged in parallel. The melamine melt from the stripping step is alternately passed to either of the cooling vessels. When the currently connected vessel is sufficiently filled, the melamine melt feed is switched over to the next vessel and the cooling step of the invention is carried out in the cooling vessel just filled. This presents the advantage that melamine melt may be passed from the stripping step to the cooling step and from the cooling step to the expansion step to be described below continuously or semicontinuously.

Once high-purity melamine is obtained by the process of the invention as set forth above, what normally follows is an expansion step in order for the product to be obtained in solid form. In a possible embodiment hereof, the melamine melt, which contains dissolved ammonia, is passed from the cooling vessel via a discharge valve to an expansion vessel. During this expansion, evaporation of ammonia brings about a temperature decrease as a result of which the heat of crystallisation of the melamine can be discharged, with high-purity melamine evolving as a solid powder. During expansion, an additional coolant, for example liquid or gaseous ammonia, may optionally be added to the expansion vessel in order to promote the cooling process. Subsequently, the solid melamine is depressurised further and cooled to room temperature for further processing.

In a preferred embodiment of the process of the invention, the stripping step is operated at a pressure below 15 MPa, which is advantageous in that the effectiveness of the stripping medium in the stripping step is further enhanced.

In another preferred embodiment of the process of the invention, not only the stripping step but also the reaction step and the gas/liquid separation step are operated at a pressure of between 5 MPa and 17 MPa, so below the pressure in the cooling step. This presents the advantage that a further decrease of the investment and operating costs is possible without the purity of the ultimately obtained melamine diminishing. More preferably, the reaction step, gas/liquid separation step and the stripping step are operated at pressures higher than 7.5 MPa, with the advantage that the reaction step may be carried out with higher efficiency, but below 15 MPa, with the advantage that the effectiveness of the stripping medium in the stripping step enhances further. Still more preferably, the pressure from the reaction step through to the stripping step is essentially the same. "Essentially the same" here means that any pressure differences within the process section mentioned are solely the result of line losses, differences in elevation and other such effects in a process plant, and in general less than 1 MPa, preferably less than 0.5 MPa.

The advantage of this is that a plant is simpler to design and operate because no provisions are needed for pressure adjustment in that part of the plant where the reaction step through to the stripping step are carried out.

The scrubber unit benefits from this, too. The unit may be of cheaper construction because, due to the lower pressure in both the gas/liquid separation step and the stripping step, the scrubbing step may be carried out at a lower pressure than the pressure in the cooling step.

A further advantage is that it is possible to combine several steps in a single piece of equipment; examples are a combination of the reaction step with the gas/liquid separation step or a combination of the gas/liquid separation step with the stripping step.

Combining the gas/liquid separation step and the stripping step in a single piece of equipment presents the advantage that the off-gases may be returned to the scrubber unit in a simpler manner.

The stripping step and the cooling step of the invention are customarily integrated in a single, whole process in which the scrubbing step, reaction step, gas/liquid separation step, stripping step and expansion step are carried out one after the other over time. However, it is also possible to apply the stripping step and the cooling step of the invention to previously prepared melamine or for melamine obtained in an alternative manner so as to improve the purity of the melamine. If the melamine to be treated is available as a solid, the melamine will need to be heated to about 370° C. in a melting step preceding the stripping step so that the melamine becomes available in liquid form; the stripping step and the cooling step may then optionally be followed by an expansion step in order for the high-purity melamine to be obtained as a solid.

The invention is elucidated by means of the following examples and comparative experiments, to which the following conditions apply:

the gas/liquid separator is integrated with the reactor 0.425 kg of $NH_3$ is metered to the stripper for each kg of melamine throughput the process conditions in comparative experiment A are chosen to be within the limits of the preferred embodiment of the known process.

TABLE 1

Process conditions

| | | Comparative Experiments | | Examples | | | |
|---|---|---|---|---|---|---|---|
| | | A | B | 1 | 2 | 3 | 4 |
| $T_r$ | (° C.) | 390 | 390 | 390 | 390 | 390 | 390 |
| $T_s$ | (° C.) | 390 | 390 | 390 | 390 | 390 | 390 |
| $T_c$ | (° C.) | 340 | 350 | 340 | 340 | 350 | 350 |
| $P_r$ | (MPa) | 25 | 22 | 25 | 9.5 | 22 | 8 |
| $P_s$ | (MPa) | 25 | 22 | 9.5 | 9.5 | 8 | 8 |
| $P_c$ | (MPa) | 25 | 22 | 25 | 25 | 22 | 22 |
| $t_r$ | (min.) | 120 | 120 | 120 | 120 | 120 | 120 |
| $t_s$ | (min.) | 90 | 90 | 90 | 90 | 90 | 90 |
| $t_c$ | (min.) | 30 | 30 | 30 | 30 | 30 | 30 |

Legend for Table 1

T=temperature, P=pressure, t=residence time. Subscripts: r=reactor, s=stripper, c=cooling vessel

TABLE 2

Product composition after cooling vessel - proportions relative to melamine

| | Comparative experiments | | Examples | | | |
|---|---|---|---|---|---|---|
| | A | B | 1 | 2 | 3 | 4 |
| Melam (% by weight) | 0.23 | 023 | 0.23 | 0.23 | 0.33 | 0.33 |
| Melem (% by weight) | 0.01 | 0.02 | 0.01 | 0.01 | 0.02 | 0.02 |
| Oxygen-containing compounds (% by weight) | 1.10 | 0.71 | 0.46 | 0.12 | 0.33 | 0.07 |

As appears from the above data, with equal ammonia metering to the stripper, the amount of oxygen-containing compounds in the melamine melt after the cooling step is lower when the stripper is operated under the conditions of the process of the invention than when the stripper is operated in accordance with the preferred embodiment of the known process.

What is claimed is:

1. Process for the preparation of melamine comprising a reaction step, a gas/liquid separation step in which a melamine melt is separated from off-gases, a stripping step and a cooling step, which comprises operating the stripping step at a pressure of between 5 MPa and 17 MPa and a temperature of between 330° C. and 450° C. and pressurizing the melamine melt obtained in the preceding steps in the cooling step to a pressure of between 15 MPa and 35 MPa, with the pressure n the cooling step being higher than the pressure in the stripping step and with the temperature in the cooling step being adjusted between the melting point of the melamine melt at the prevailing temperature and 365° C.

2. Process according to claim 1, wherein the stripping step is carried out at a pressure which is at least 1.5 MPa lower than the pressure in the cooling step.

3. Process according to claim 1, wherein the stripping step is carried out in two or more cooling vessels arranged in parallel.

4. Process according to claim 1, wherein the stripping step is carried out at a pressure of between 5 and 15 MPa.

5. Process according to claim 1, wherein the reaction step and the gas liquid separation step are operated at a pressure of between 5 MPa and 17MPa and a temperature of between 330° C. and 450° C.

6. Process according to claim 5, wherein the reaction step, the gas/liquid separation step and the stripping step are operated at a pressure of between 7.5 MPa and 15 MPa.

7. Process according to claim 6, wherein pressure in the reaction step and the gas/liquid separation step differs from the pressure in the stripping step by less than 1 MPa.

* * * * *